(12) United States Patent
Chen

(10) Patent No.: US 9,044,551 B2
(45) Date of Patent: Jun. 2, 2015

(54) SAFETY SYRINGE

(71) Applicant: Cho-Ying Chen, Taichung (TW)

(72) Inventor: Cho-Ying Chen, Taichung (TW)

(73) Assignees: HSIAO I FAN, Taichung (TW); LEE HSHIN CHUNG, Taoyuan (TW)

( * ) Notice: Subject to any disclaimer, the term of this patent is extended or adjusted under 35 U.S.C. 154(b) by 170 days.

(21) Appl. No.: 13/633,678

(22) Filed: Oct. 2, 2012

(65) Prior Publication Data

US 2013/0116619 A1    May 9, 2013

(30) Foreign Application Priority Data

Nov. 7, 2011  (TW) .............................. 100140541 A

(51) Int. Cl.
*A61M 5/00* (2006.01)
*A61M 5/32* (2006.01)

(52) U.S. Cl.
CPC ......... *A61M 5/322* (2013.01); *A61M 2005/323* (2013.01)

(58) Field of Classification Search
CPC ....................... A61M 2005/323; A61M 5/322
USPC .................. 604/110, 162, 192, 195, 197, 187
See application file for complete search history.

(56) References Cited

U.S. PATENT DOCUMENTS

| 5,211,628 A | 5/1993 | Marshall |
| 5,382,235 A | 1/1995 | Sak |
| 5,993,417 A | 11/1999 | Yerfino et al. |
| 7,179,243 B2 * | 2/2007 | Chen ............................ 604/110 |

FOREIGN PATENT DOCUMENTS

| CN | 101104087 A | 1/2008 |
| CN | 10124921 B | 6/2010 |
| TW | M360049 | 7/2009 |

* cited by examiner

*Primary Examiner* — Rebecca E Eisenberg
(74) *Attorney, Agent, or Firm* — Muncy, Geissler, Olds & Lowe, P.C.

(57) ABSTRACT

A safety syringe includes a barrel, a plunger, and a needle hub. The barrel is extended axially and includes a first tube portion, a second tube portion extended from an end of the first tube portion, and a first folded ring flexibly branched and formed on an inner side of the first tube portion and disposed around the axis, such that after the first folded ring is unfolded, the first folded ring is bounded and extended from the first tube portion towards the second tube portion, and includes a movable first flexible portion. The plunger includes a rod extended along the axis. The needle hub is detachably installed in second tube portion. The plunger can be moved to an injecting position, a limit position, and a disposal position with respect to the needle hub.

7 Claims, 10 Drawing Sheets

SAFETY SYRINGE

FIELD OF THE INVENTION

The present invention relates to a syringe, in particular to the safety syringe.

BACKGROUND OF THE INVENTION

Prior Taiwan application number 098201291, entitled "Disposable safety syringe structure," was invented by the inventor of the present invention. In FIGS. 9 and 10 of prior Taiwan application number 098201291, the disposable safety syringe structure comprises a barrel 10, a needle hub 11 movably installed in the barrel 10, a plunger 12 movably inserted into the barrel 10 and having a plug head 121, and two positioning bases 101 disposed in the barrel 10 and having a snap slot 102 each, wherein the needle hub 11 has a connecting section 111, an elastic hook plate 112, and two protruding columns 113 corresponding to the snap slots 102 respectively and having a snap member 114 each. In the assembling process, the needle hub 11 is installed into the barrel 10, and the snap members 114 of the protruding columns 113 are embedded into the snap slots 102 respectively to achieve the positioning effect.

However, the aforementioned conventional safety syringe requires a precise embedment of the snap members 114 into the snap slots 102 to achieve the positioning effect, so that it takes a longer time for the installation process. Obviously, the conventional safety syringe requires further improvements. On the other hand, the needle hub 11, the plunger 12, and the barrel 10 are manufactured by plastic injection molding, so that the protruding columns 113 of needle hub 11 require a more complicated mold for the manufacture, and incur a higher cost.

SUMMARY OF THE INVENTION

Therefore, it is a primary objective of the present invention to overcome the shortcomings of the prior art by providing a safety syringe having the features of easy assembling and low cost.

To achieve the foregoing objective, the present invention to provide a safety syringe comprising a barrel, a plunger, and a needle hub.

The barrel is extended along an axial direction and includes a first tube portion, a second tube portion extended from an end of the first tube portion, and a first folded ring flexibly formed on an inner side of the first tube portion and disposed around the axis, and after the first folded ring is unfolded, the first folded ring is bounded and extended from the first tube portion towards the second tube portion and includes a movable first flexible portion.

The plunger includes a rod disposed along the axis and movably inserted into the barrel, and a plug installed at an end of the rod.

The needle hub is detachably installed in second tube portion, wherein the plug of the plunger can be snapped into the needle hub to spread open the first flexible portion, so that the first flexible portion can be separated from the needle hub.

The present invention has the following advantages and effects. The first folded ring and the second tube portion can position the needle hub effectively to provide a convenient installation. On the other hand, the needle hub of the invention has a simpler shape than the conventional one, so as to lower the manufacturing cost significantly.

DESCRIPTION OF THE PREFERRED EMBODIMENTS

Figure 1:
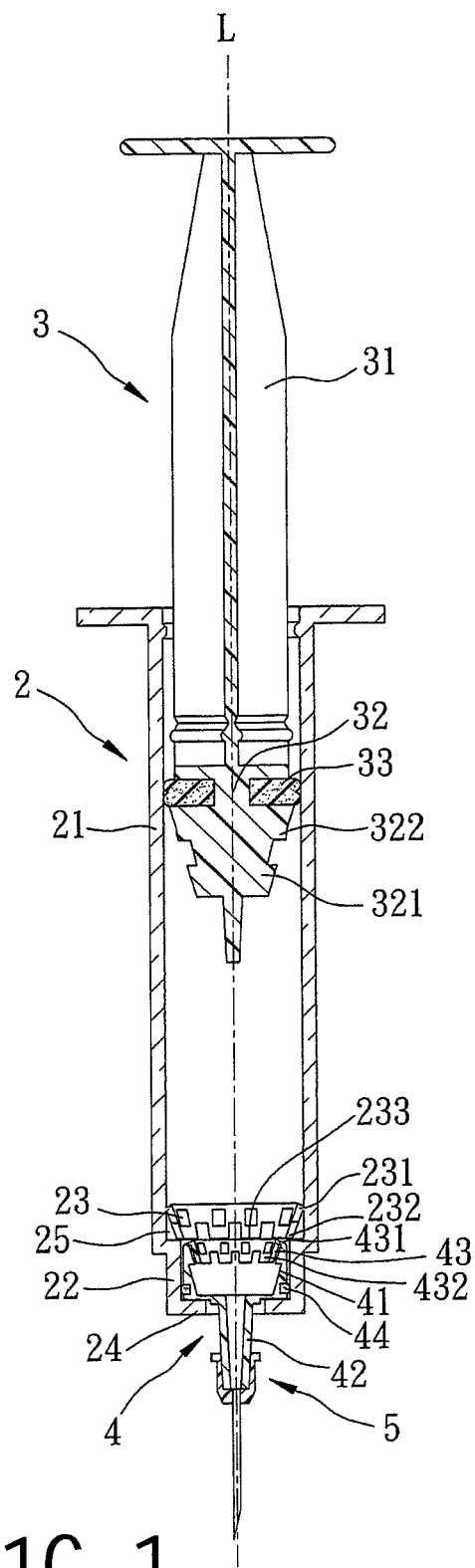
FIG. 1 is a cross-sectional side view of a safety syringe in accordance with a first preferred embodiment of the present invention, showing an injecting position of a plunger.

The technical characteristics of the present invention will become apparent with the detailed description of the preferred embodiments accompanied with the illustration of related drawings as follows. It is noteworthy that same numerals are used for representing the same respective elements in the drawings, and the drawings are provided for the purpose of illustrating the invention, but not intended for limiting the scope of the invention.

With reference to FIG. 1 for a safety syringe in accordance with the first preferred embodiment of the present invention, the safety syringe comprises a barrel 2, a plunger 3, and a needle hub 4.

Figure 2:
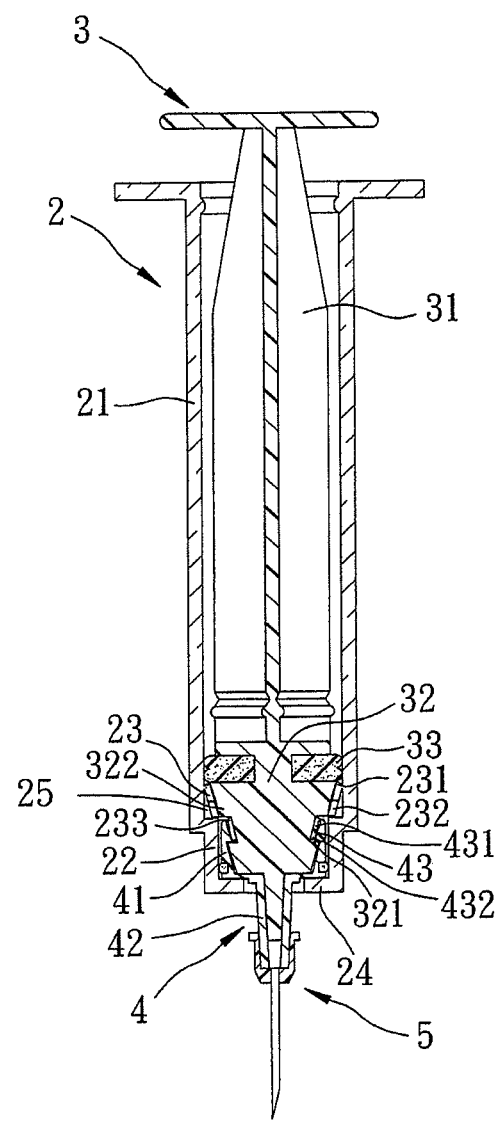
FIG. 2 is a cross-sectional side view of a safety syringe in accordance with the first preferred embodiment of the present invention, showing a limit position of a plunger.
Figure 3:
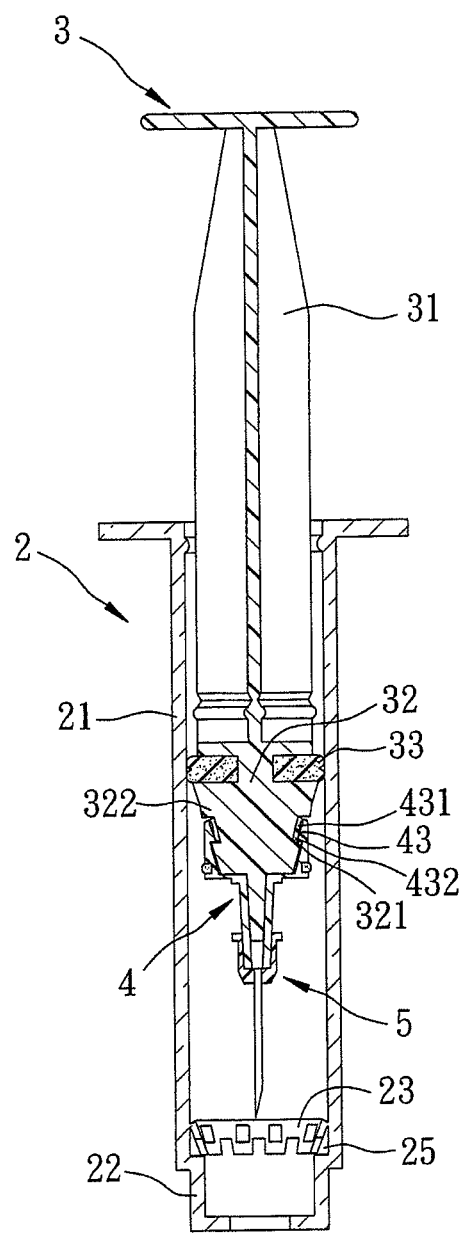
FIG. 3 is a cross-sectional side view of a safety syringe in accordance with the first preferred embodiment of the present invention, showing a disposal position of a plunger.

With reference to FIGS. 1, 2 and 3, the barrel 2 is extended in the direction of an axis L and includes a first tube portion 21, a second tube portion 22 extended from an end of the first tube portion 21, a first folded ring 23 flexibly branched and formed on an inner side of the first tube portion 21 and disposed around the axis L, a positioning ring 24 installed on an internal side of the second tube portion 22, and a storage space 25 formed between the first tube portion 21 and the second tube portion 22, wherein the barrel of the second tube portion 22 has an internal diameter smaller than the internal diameter of the barrel of the first tube portion 21.

After the first folded ring 23 is unfolded, the first folded ring 23 is bounded and extended from the first tube portion 21 towards the second tube portion 22 and has a first ring base 231 disposed in the first tube portion 21 and around the axis L, and a first flexible portion 232 movably disposed at a position opposite to the first ring base 231 and having an opening 233. Wherein, the first flexible portion 232 has a plurality of square notches formed at an end of the first flexible portion 232 and disposed with an interval apart from one another.

The plunger 3 further includes a rod 31 disposed along the axis L and movably inserted into the barrel 2, a plug 32 installed at an end of the rod 31, and a piston plate 33 installed around the plug 32.

The plug 32 of the plunger 3 has a circular flange 321, and an expansion ring 322 installed between the piston plate 33 and the circular flange 321.

The needle hub 4 is detachably installed in second tube portion 22 and includes a main body 41 movably disposed in the second tube portion 22 and abutted against the positioning ring 24, a sheath tube 42 installed at the bottom of the main body 41 and passed through the positioning ring 24, a second folded ring 43 bounded and extended from a top edge of the main body 41 towards the sheath tube 42, and a leakproof ring 44 detachably installed around the main body 41.

The second folded ring 43 has a second ring base 431 disposed at the main body 41 and around the axis L, and a second flexible portion 432 disposed around the axis L and opposite to the second ring base 431.

Figure 4:
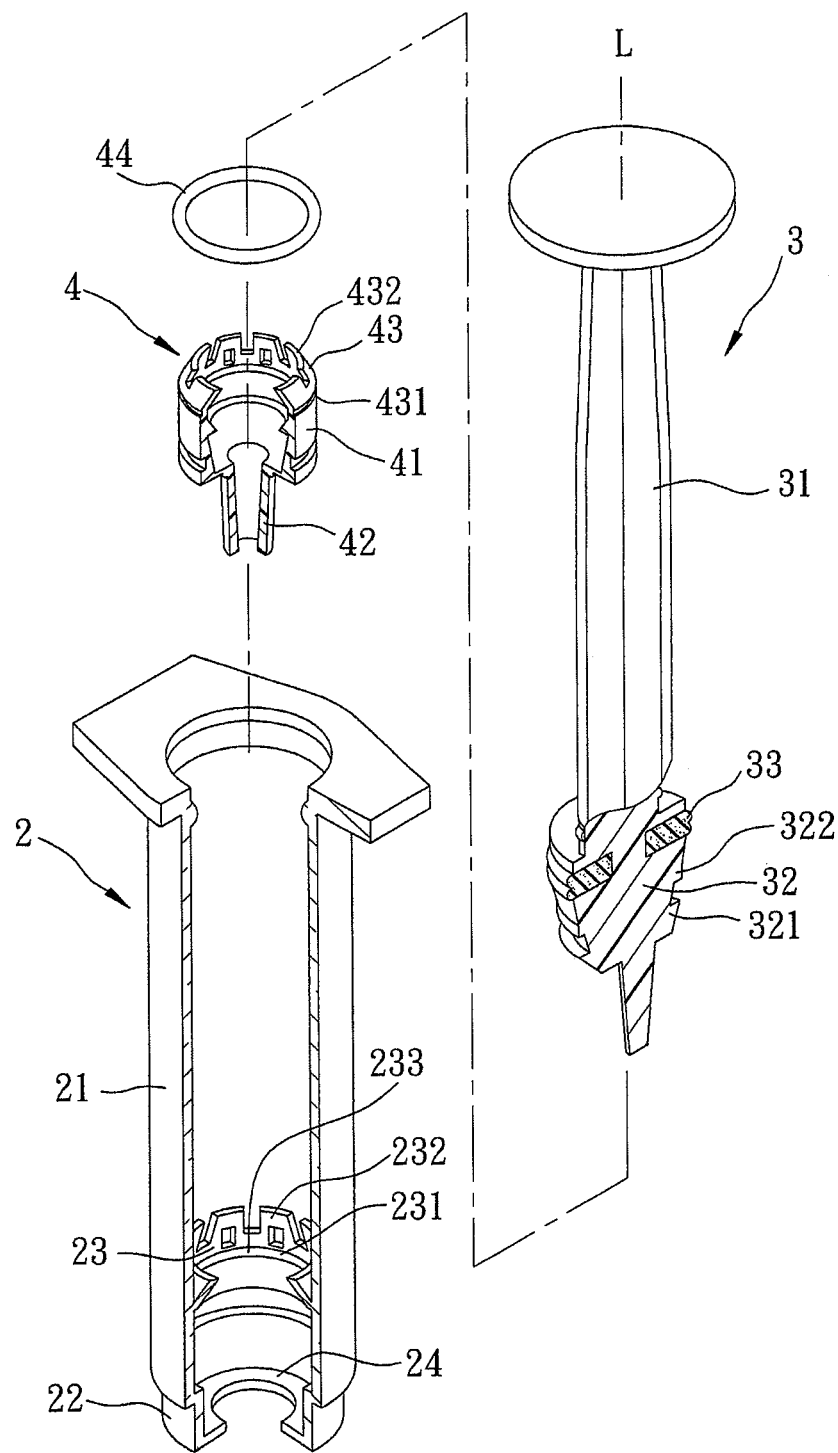
FIG. 4 is an exploded view of the first preferred embodiment of the present invention, showing a first folded ring of a barrel and a second folded ring of a needle hub not being bent after a plastic injection molding process.
Figure 5:
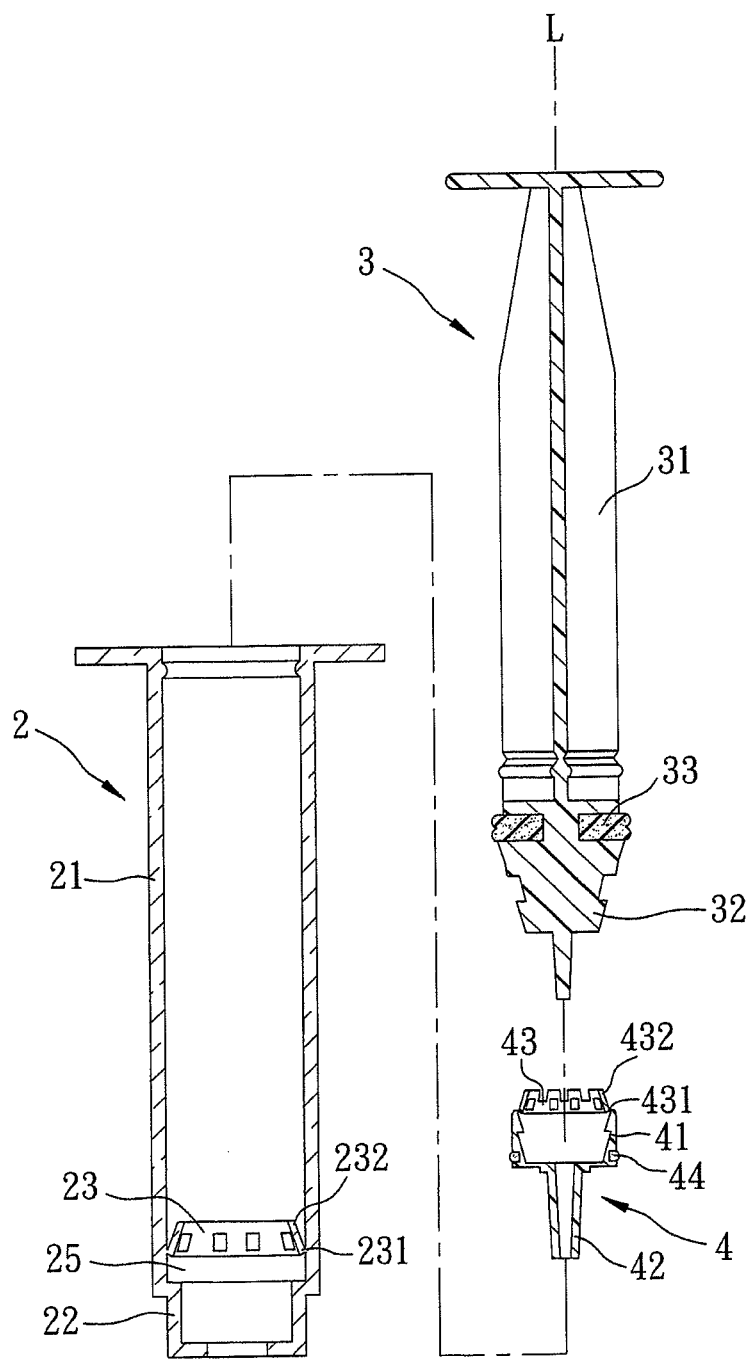
FIG. 5 is a cross-sectional exploded view of the first preferred embodiment of the present invention, showing a first folded ring and a second folded ring not being bent after a plastic injection molding process.

In FIGS. 4 and 5, the barrel 2, the plunger 3, and the needle hub 4 are formed by plastic injection molding during an assembling process, so that the first flexible portion 232 and the second flexible portion 432 face upward and are disposed at positions away from the second tube portion 22 to facilitate the de-molding process.

Figure 6:
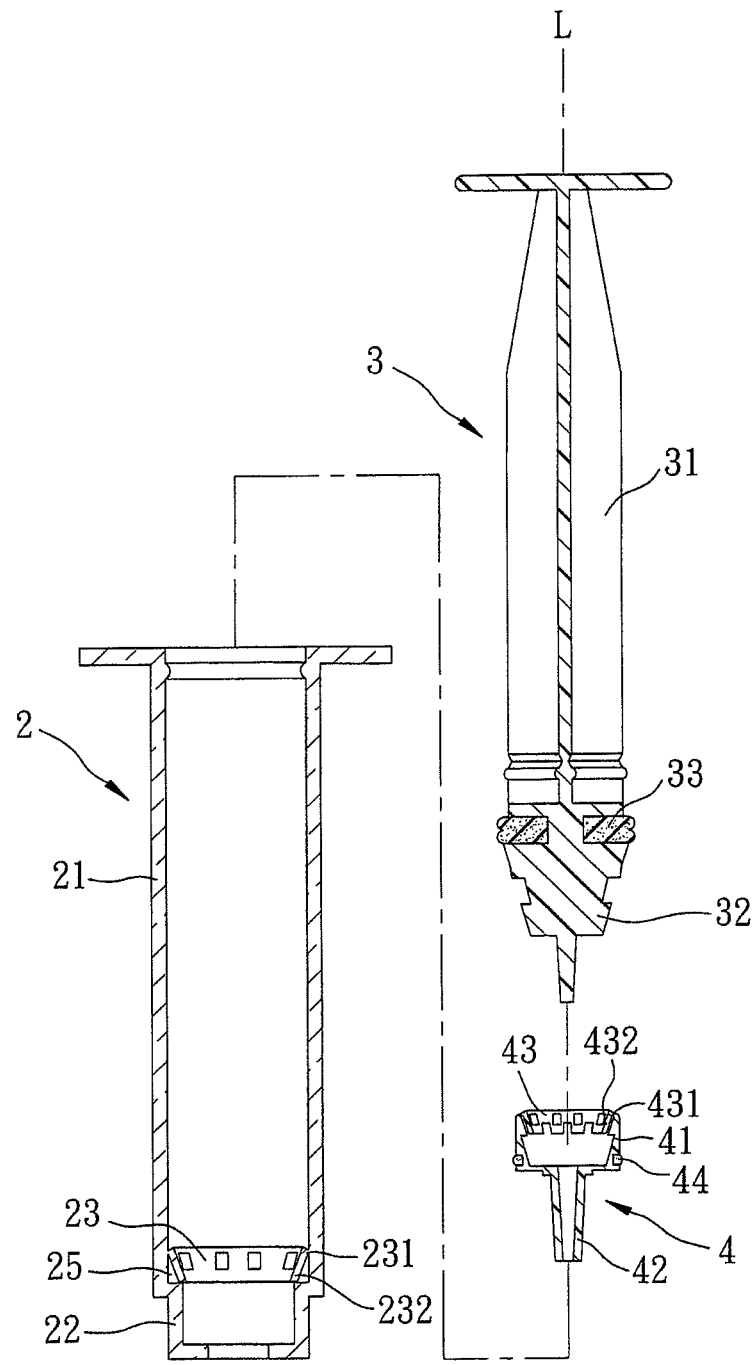
FIG. 6 is a cross-sectional exploded view of the first preferred embodiment of the present invention, showing a first folded ring and a second folded ring being bent after a plastic injection molding process.

In FIGS. 6 and 1, the piston plate 33 is sheathed on the plug 32 of the plunger 3, and the leakproof ring 44 is sheathed on the main body 41 of the needle hub 4. The first flexible portion 232 of the barrel 2 is bent towards the second tube portion 22, and the second flexible portion 432 of the needle hub 4 is bent towards the internal side of the main body 41. And then, the needle hub 4 is placed into the second tube portion 22 of the barrel 2, and the first flexible portion 232 of the first folded ring 23 is abutted against the second ring base 431 of the second folded ring 43 to prevent the needle hub 4 from sliding towards the first tube portion 21, and then the plug 32 of the plunger 3 is inserted into the first tube portion 21. Finally, a needle 5 is sheathed on the sheath tube 42 of the main body 41 to complete the installation.

In FIGS. 1, 2 and 3, when use, the plunger 3 can be moved to an injecting position, a limit position, and a disposal position with respect to the needle hub 4 in order to squeeze the medicine in the barrel 2 out from the sheath tube 42 of the needle hub 4, and then the needle 5 is hidden in the first tube portion 21.

At the injecting position, the plug 32 of the plunger 3 is situated in the first tube portion 21, and the piston plate 33 of the plug 32 and the first ring base 231 of the first folded ring 23 are separated with an interval apart and the first flexible portion 232 is abutted against the second ring base 431 of the second folded ring 43 to push the needle hub 4 to be fixed into the second tube portion 22, and the circular flange 321 of the plug 32 is not passed into the main body of the needle hub 4. At the limit position, an end of the piston plate 33 of the plug 32 is abutted against the first ring base 231, and the circular flange 321 of the plug 32 is passed into the main body 41 of the needle hub 4 and engaged with the second flexible portion 432, and an expansion ring 322 pushes the flexible portion 232 into the storage space 25 and stretches open an opening 233 of the first flexible portion 232 to separate the first flexible portion 232 from the needle hub 4. After the circular flange 321 is snapped to the second flexible portion 432, a user can retract the plunger 3 away from the second tube portion 22 to drive the needle hub 4 to be released from the first folded ring 23 and moved towards the first tube portion 21 in order to separate from the second tube portion 22, so that the needle 5 will be stored in the first tube portion 21 and situated at the disposal position to prevent the needle 5 from accidental puncture.

Figure 7:
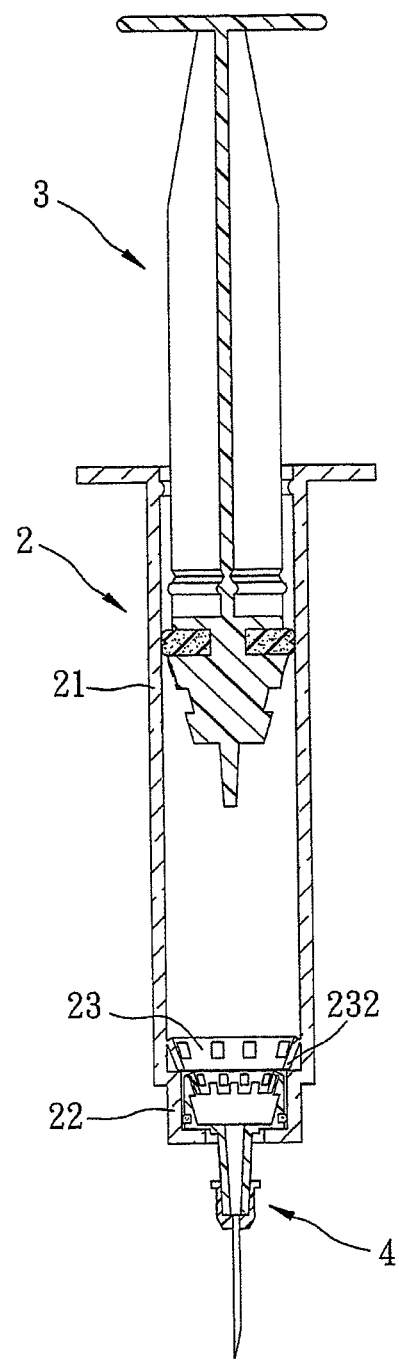
FIG. 7 is a cross-sectional view of a safety syringe in accordance with a second preferred embodiment of the present invention.

With reference to FIG. 7 for a safety syringe in accordance with the second preferred embodiment of the present invention, this preferred embodiment is substantially the same as the first preferred embodiment, except that an end of the first flexible portion 232 of this embodiment has an even shape.

Figure 8:
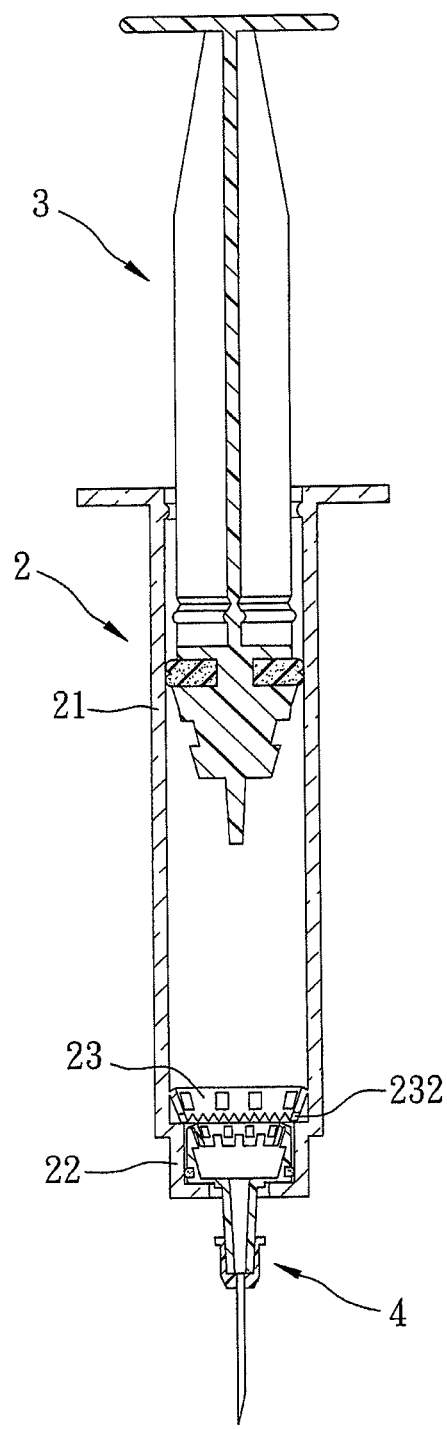
FIG. 8 is a cross-sectional view of a safety syringe in accordance with a third preferred embodiment of the present invention.
Figure 9:
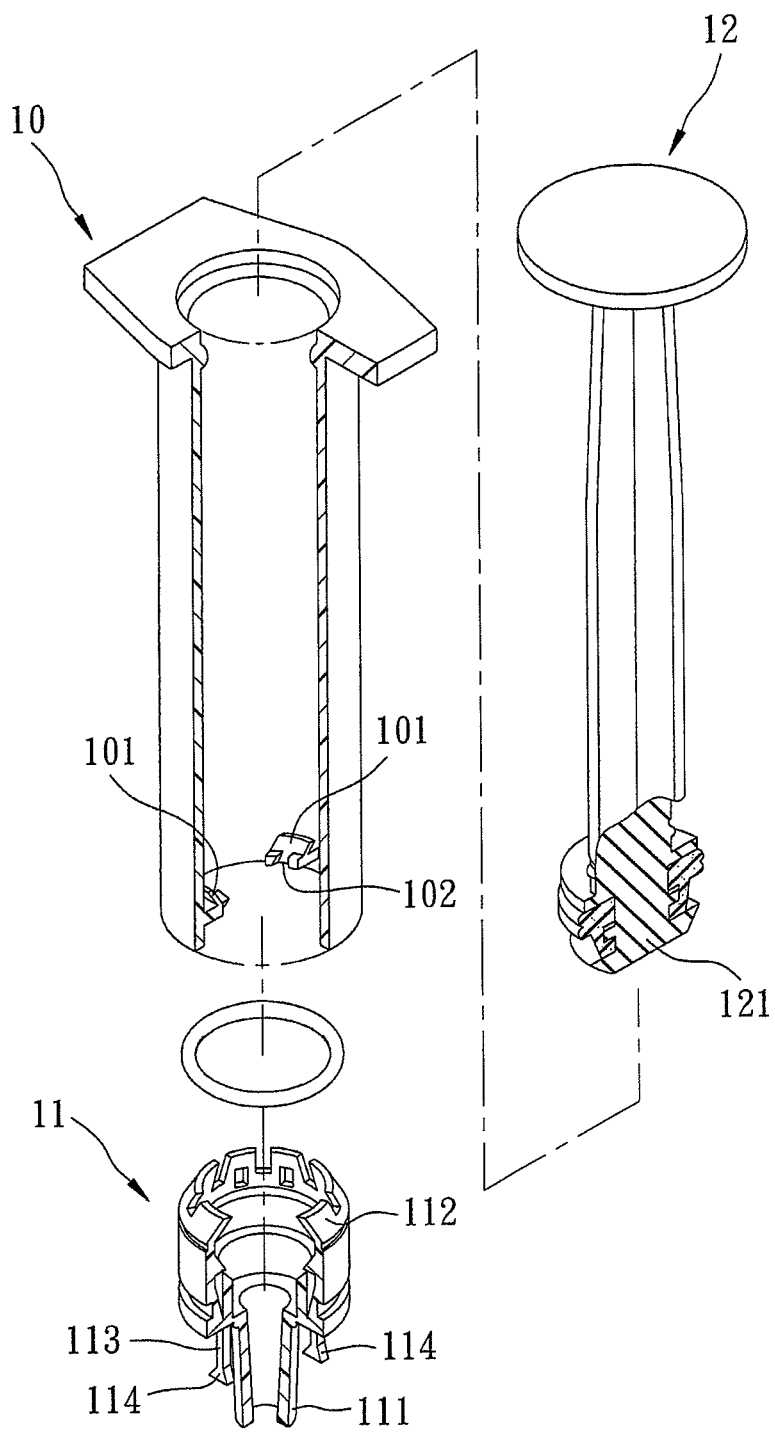
FIG. 9 is an exploded view of a conventional safety syringe.
Figure 10:
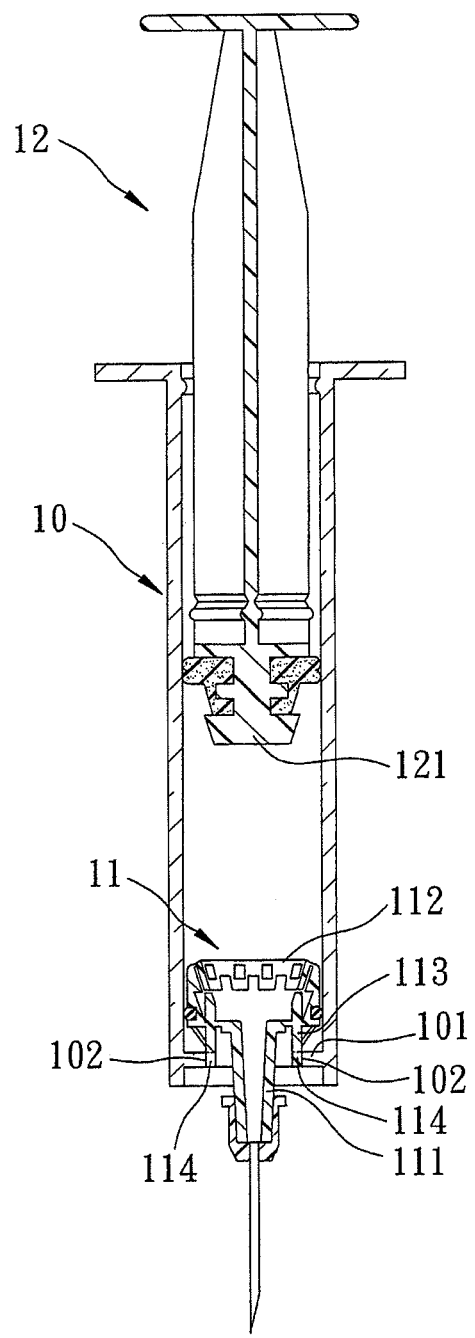
FIG. 10 is a cross-sectional view of a conventional safety syringe.

With reference to FIG. 8 for a safety syringe in accordance with the third preferred embodiment of the present invention, this preferred embodiment is substantially the same as the first preferred embodiment, except that the first flexible portion 232 of this embodiment has a plurality of serrated notches.

In summation, the safety syringe of the present invention has the following advantages and effects:

The assembling process no longer requires a precise alignment of the needle hub 4 with the second tube portion 22 in order to position the first folded ring 23 effectively. The invention can provide a very convenient assembling process. On the other hand, the needle hub 4 no longer requires a high precision of the protruding column 113 as required in the prior art, so that the manufacturing cost can be reduced significantly.

It is noteworthy that the barrel of the first tube portion 21 can have an internal diameter equal to the internal diameter of the barrel of the second tube portion 22 to make the manufacture more easily and further lower the production cost.

What is claimed is:
1. A safety syringe, comprising:
a barrel, extended in a direction of an axis, and including a first tube portion, a second tube portion extended from an end of the first tube portion, and a first folded ring including a movable first flexible portion, the first folded ring flexibly branched and formed on an inner side of the first tube portion and disposed around the axis, such that after the first folded ring is unfolded, the first folded ring is bounded and extended from the first tube portion with the first flexible portion extending away from the second tube portion;
a plunger, including a rod extended along the axis and movably inserted into the barrel, and a plug installed at an end of the rod; and
a needle hub, detachably installed in the second tube portion adjacent to the first flexible portion in the first tube portion, with a second folding ring including a second flexible portion installed inside the needle hub, and the plug of the plunger being configured to be snapped into the needle hub and configured to compress the first flexible portion against the inner side of the first tube portion, so that the first flexible portion is separated from the needle hub,
wherein the plunger can be moved to an injecting position, a limit position, and a disposal position with respect to the needle hub, and when the plunger is moved to the injecting position, the plug of the plunger is situated in the first tube portion and apart from the needle hub, and the first flexible portion abuts the needle hub thereby fixing the needle hub in the second tube portion, and when the plunger is moved to the limit position, the plug is snapped into the needle hub to compress the first flexible portion against the inner side of the first tube portion, so that the first flexible portion is separated from the needle hub, and when the plunger is moved to the disposal position, the plunger is situated away from the second tube portion, and the needle hub is released from the first folded ring and separated from the second tube portion, wherein the second tube portion has an internal diameter smaller than the internal diameter of the barrel of the first tube portion, and the barrel of the second tube portion further has a storage space formed between the first tube portion and the second tube portion for accommodating the first flexible portion, and at the limit position, the first flexible portion is pushed by the plug into the storage space.

2. The safety syringe of claim 1, wherein the barrel further includes a positioning ring disposed on an internal side of the second tube portion, and the needle hub includes a main body movably installed in the second tube portion and abutted against the positioning ring, a sheath tube disposed at the bottom of the main body and passed through the positioning ring, the second folded ring is bounded and extended from a top edge of the main body towards the sheath tube, and a leakproof ring installed around the main body.

3. The safety syringe of claim 2, wherein the first folded ring further has a first ring base disposed on an internal side of the first tube portion and opposite to the first ring base, and the second folded ring has a second ring base disposed at the main body and around the axis, and a second flexible portion disposed around the axis and opposite to the second ring base.

4. The safety syringe of claim 3, wherein the plunger further has a piston plate disposed around the plug, and the plug of the plunger has a circular flange, and an expansion ring disposed between the piston plate and the circular flange, such that at the limit position, an end of the piston plate is abutted against the first ring base, and the circular flange is passed into the main body and engaged with the second flexible portion, and the expansion ring stretches open the first flexible portion.

5. The safety syringe of claim 1, wherein the first flexible portion has a plurality of square notches disposed with an interval apart from one another.

6. The safety syringe of claim 1, wherein the first flexible portion has an end that is non-serrated.

7. The safety syringe of claim 1, wherein the first flexible portion has a plurality of serrated notches.

* * * * *